United States Patent
De La Paz et al.

(10) Patent No.: US 7,314,720 B2
(45) Date of Patent: Jan. 1, 2008

(54) METHOD OF DIAGNOSING NON-ALCOHOLIC STEATOHEPATITIS (NASH) USING MOLECULAR MARKERS

(75) Inventors: José María Mato De La Paz, Madrid (ES); Fernando Corrales Izquierdo, Pamplona (ES); Enrique Santa María Martínez, Pamplona (ES)

(73) Assignee: One Way Liver Genomic, S.L., Madrid (ES)

( * ) Notice: Subject to any disclaimer, the term of this patent is extended or adjusted under 35 U.S.C. 154(b) by 0 days.

(21) Appl. No.: 10/540,212

(22) PCT Filed: Dec. 16, 2003

(86) PCT No.: PCT/ES03/00635

§ 371 (c)(1),
(2), (4) Date: Jan. 12, 2006

(87) PCT Pub. No.: WO2004/055520

PCT Pub. Date: Jul. 1, 2004

(65) Prior Publication Data

US 2006/0135420 A1    Jun. 22, 2006

(30) Foreign Application Priority Data

Dec. 18, 2002    (ES) ................................ 200202911

(51) Int. Cl.
*G01N 33/53* (2006.01)

(52) U.S. Cl. ...................... 435/7.1; 435/7.2; 435/7.21; 436/518; 436/287.1

(58) Field of Classification Search ........... 435/4–7.95, 435/23; 514/438; 356/128, 400, 401, 509, 356/620; 257/82–84; 359/237, 245, 333, 359/345–347, 558, 566; 372/6, 11, 33; 436/518, 436/287.1

See application file for complete search history.

(56) References Cited

U.S. PATENT DOCUMENTS

2006/0084057 A1* 4/2006 Rose et al. .................... 435/6

OTHER PUBLICATIONS

Lonardo et al. Hepatology 2002 vol. 36, p. 514-515.*
Lu, S.C., et al. "Methionine Adenosyltransferase 1A Knockout Mice are Predisposed to Liver Injury and Exhibit Increased Expression of Genes Involved in Proliferation". PNAS, May 8, 2001, vol. 98, No. 10, p. 5560-5565.
Mato, J.M., et al. "S-Adenosylmethionine: A Control Switch That Regulates Liver Function" FASEB Journal, vol. 16, Jan. 2002, pp. 15-26.
Zatloukal, K., et al. "Alcoholic and Nonalcoholic Steatohepatitis" Rev. Esp. Patoi., vol. 32, No. 3, 1999, pp. 293-294.

(Continued)

*Primary Examiner*—Long V. Le
*Assistant Examiner*—Nelson Yang
(74) *Attorney, Agent, or Firm*—Steven J. Hultquist; Intellectual Property/Technology Law (57) ABSTRACT

The invention relates to a method of diagnosing non-alcoholic steatohepatitis (NASH) using molecular markers. The inventive method consists in detecting and quantifying, in vitro in a hepatic tissue sample, the levels of a protein which can be used as a NASH molecular marker and which is selected from apolipoprotein A1, sub-unit β of the mitochondrial ATPase, leukotriene A4 hydrolase, keratin 18, guanidine acetate N-methyltransferase, superoxide dismutase, albumin, antioxidant protein 2 (isoform 1), prohibitin 1, methionine adenosyl transferase, long-chain acyl CoA dehydrogenase, selenium binding protein, antioxidant protein 2 (isoform 2), and combinations of same. The invention further consists in comparing the results obtained with the normal values of said proteins in healthy hepatic tissue. Said method can be used to diagnose NASH and/or to assess a patient's potential risk of developing NASH.

8 Claims, 5 Drawing Sheets

OTHER PUBLICATIONS

Santamaria, E., et al. "Functional Proteomics of Nonalcoholic Steatohepatitis: Mitochondrial Proteins as Targets of S-adenosylmethionine" PNAS, vol. 100, No. 6, Mar. 18, 2003, pp. 3065-3070.

Sanyal, Arun J., AGA technical review on nonalcoholic fatty liver disease, Gastroenterology, Nov. 2002, pp. 1705-1725, vol. 123, No. 5.

* cited by examiner

METHOD OF DIAGNOSING NON-ALCOHOLIC STEATOHEPATITIS (NASH) USING MOLECULAR MARKERS

CROSS-REFERENCE TO RELATES APPLICATIONS

This application is filed under the provision of 35 U.S.C. §371 and claims the priority of International Patent Application No. PCT/ES03/000635 filed Dec. 16, 2003, which in turn claims priority of Spanish Patent Application No. P200202911 filed Dec. 18, 2002.

FIELD OF THE INVENTION

In general, the invention is related to the diagnosis of non-alcoholic steatohepatitis (NASH), more specifically, to the early diagnosis for the susceptibility of a person to develop NASH or its confirmation in already diagnosed patients: in both cases the diagnosis is based on the identification of molecular markers of NASH and/or the analysis of the expression patterns of said molecular markers of NASH in liver.

BACKGROUND OF THE INVENTION

Non-alcoholic steatohepatitis (NASH) is a severe liver lesion that is characterized by necrosis, inflammation and fibrosis. NASH and alcoholic steatohepatitis (ASH) are histologically indistinguishable and are thought to have the same etiology. Nowadays, NASH is considered to be a progressive disease with 25% incidence of cirrhosis and 10%-15% incidence of mortality. It is also believed to cause liver disease in most cases of cryptogenic cirrhosis (unknown cause). Therefore, research on NASH has become one of the subjects with top priority in clinical hepatology. NASH epidemiology, characteristics, diagnosis strategies and treatment have been reviewed by Andrea E. Reid [Reid A. E., Gastroenterology, 2001, 121:710-723].

To illustrate the problem, some epidemiological data could be enumerated:
- between 7% and 11% of the patients who undergo an liver biopsy in the United States and Canada are diagnosed with NASH;
- between 60% and 83% of the patients diagnosed with NASH are women;
- by 30% of the obese patients suffer from NASH;
- fibrosis appearance is detected in 43% of patients with NASH;
- cirrhosis incidence in patients with NASH is approximately 25%;
- all the patients who develop alcoholic cirrhosis (approximately 50% out of all cirrhosis cases) have previously developed ASH; and
- NASH is frequent in patients with hepatitis C.

Due to the prominent position of NASH among chronic and progressive liver diseases, there is an increasing interest in the determination of its pathogenesis. However, pathophysiological mechanisms leading to NASH development have not been determined yet. Alcoholic people may have a moderately fatty liver for many years and, without a change in their drinking habits, suddenly develop severe alcoholic hepatitis. In the same way, obesity, type II diabetes and hypertriglyceridemia are frequently associated with fat accumulation in liver and, although this situation does not invariably lead to the development of necroinflammatory lesions, these patients are at higher risk to develop NASH. Consequently, the existence of environmental or cellular factors working as inhibitors of a cascade of molecular events inducing necrosis, inflammation and fibrosis have been proposed. Portal endotoxemia and lipid peroxidation are two of these possible factors. Alterations in the expression of different genes/proteins, such as CYP2E1, CYP4A, UCP2, have also been identified in NASH and ASH; however, none of these genes have a value for the diagnosis or prediction of the development of the disease in time.

Nowadays, most NASH patients are examined due to high, chronic results in liver function analysis (e.g., moderate chronic increase of aminotransferases), hepatomegalya, or both. A combination of the clinical history, physical examination, blood analysis and radiological and histological examinations exclude other causes of liver disease. Blood analysis has to include a complete liver profile including, for example, blood cell count and anti-HCV antibodies, hepatitis B surface antigen, hepatic iron index, ceruloplasmin, antinuclear antibody, $\alpha_1$-antitrypsin and anti-mitochondrial antibody determination. Image diagnosis, for example with liver ultrasonography (the preferred modality of image diagnosis), reveals the existence of a "shiny" liver with increased ecogenity. Nevertheless, this technique sensitivity and specificity for steatosis are 89%-95% and 84-93% respectively. Fatty liver diagnosis can also be diagnosed by computerized tomography or by abdominal magnetic resonance. In any case, clinical, analytical and radiological data do not allow the differentiation of NASH and alcoholic hepatitis given that both pathologies are histologically identical (presence of diffuse or centrilobular macrovesicular steatosis, ballooned hepatocytes, necrosis, mixed lobular inflammatory infiltration, with or without necrosis, Mallory bodies, lipogranulomes and glycogenic nuclei). Therefore, the diagnosis of NASH is only confirmed in the cases of significant alcohol intake absence (typically lower than 20-40 g alcohol/day). Up to now, the proposed molecular markers (CYP2E1, CYP4A, UCP2) do not have a value for the diagnosis or prediction of the development of the disease in time.

Therefore, it is necessary to have tools to study NASH progression in time and to identify molecular markers associated with NASH. One of these tools could be an animal model which allowed the analysis of the patterns of genes and proteins in a normal liver and in a liver with NASH, as well as along the disease progression in time. Identification of these molecular markers, particularly early molecular markers, with a diagnosis and predictive value for NASH, and the study of their functional effects, would help prevent and/or treat NASH. Their identification would also help search and develop useful drugs for preventive and/or curative treatment of this disease. A good molecular marker of NASH would appear early in the liver, long before histological alterations were observed. Ideally, to efficiently diagnose the predisposition to suffer from NASH, it would be better to have a group of early molecular markers of NASH appearance than to have only one. This group of molecular markers would be something like the early "fingerprint" of the disease.

In this research line, a model for the in vivo study of NASH has been developed. This model is based on a knockout mouse deficient in MAT1A gene, that is, in S-adenosylmethionine (AdoMet) synthesis in liver, an essential cellular metabolite, named MATO (Lu S. C., et al., Proc. Natl. Acad. Sci. USA, 2001; 98:5560-5565). In addition to NASH, these MATO mice spontaneously develop oxidative stress and hepatocellular carcinoma (Martínez-Chantar M. L., et al., Faseb J., 2002, 16:1292-1294). MAT1A gene is specifically expressed in adult livers, although it has been demonstrated that the expression of this gene is silent in patients with hepatic cirrhosis (both alcoholic and non-alcoholic). 3-month-old MATO mice livers are normal but they are much more liable to develop severe macrovesicular steatosis (induced by a choline-deficient diet) and necrosis (induced by $CCl_4$); at 8 months, MATO mice spontaneously develop NASH; and at 14-18 months they are at high risk to develop hepatocellular carcinoma (more than 80% of the animals develop hepatic tumours). Preliminary DNA microarray assays (Lu S. C., et al., Proc. Natl. Acad. Sci. USA, 2001; 98:5560-5565) show that at 3 months of age (when the histology of the liver is still normal), there are already hundreds of differences in gene and protein expression between normal or wild type (WT) and MATO mice. That is to say that long before an histological lesion is observed in the liver, NASH has already started to develop at a molecular level, although many of said differences do not remain throughout the progression of the disease.

SUMMARY OF THE INVENTION

One purpose of this invention is the development of a method for the diagnosis of NASH based on the analysis of the expression patterns of certain proteins which work as molecular markers of said disease in liver.

To identify NASH molecular markers and obtain the fingerprint of said disease, the inventors have analyzed the differential expression of proteins by means of proteomic techniques (two-dimensional electrophoresis and identification of the differentially expressed proteins by mass spectrometry) in liver samples from WT and MATO mice [mutant knockout mice deficient in MAT1A gene (MAT-/-)] (Lu S. C., et al., Proc. Natl. Acad. Sci. USA, 2001; 98:5560-5565) in time (1 and 15 days, 3 and 8 months old) until the appearance of NASH. Said MATO mutant mice were chosen because they could be used to study the presence of NASH molecular markers before the disease was evident at a histological level.

All mice were fed a normal diet. NASH appearance and evolution was followed up by histological control. The analysis of this information allowed the identification of proteins whose expression is altered (up- or down-regulated) from the first day after the birth of a subject susceptible of developing NASH until NASH appearance. These proteins, useful as NASH molecular markers, are the following: apolipoprotein A1, mitochondrial ATPase β subunit, leukotriene $A_4$ hydrolase, keratin 18, guanidinoacetate N-methyltransferase, superoxide dismutase, albumin, antioxidant protein 2 (isoform 1), prohibitin 1, methionine adenosyl transferase, long-chain acyl-CoA dehydrogenase, selenium binding protein and antioxidant protein 2 (isoform 2). Apolipoprotein A1, mitochondrial ATPase β subunit, leukotriene $A_4$ hydrolase, keratin 18, guanidinoacetate N-methyltransferase, superoxide dismutase, albumin and antioxidant protein 2 (isoform 1) are up-regulated in the liver while prohibitin 1, methionine adenosyl transferase, long-chain acyl-CoA dehydrogenase, selenium union protein and antioxidant protein 2 (isoform 2) are down-regulated, months before the appearance of NASH in MATO mice livers. These proteins might be used as molecular markers of the risk of development of NASH, isolated or combined, considering expression patterns of all or part of said proteins, to determine NASH fingerprint.

Apolipoprotein A1 (APA1) is the protein component of a lipoprotein that carries lipids in blood. Variations in APA1 levels associated to hepatic fibrosis have been described [Teare J. P., et al., Lancet (North American Edition), 1993, 342:895-898].

Mitochondrial ATPase β subunit (ATPB) is a component of mitochodrial ATPase (or mitochondrial ATP synthase), that catalyses ATP synthesis from ADP and inorganic phosphorous in mitochondria using the energy derived from a proton gradient.

Leukotriene $A_4$ hydrolase or LKHA is an enzyme involved in leukotriene biosynthesis and is a marker for inflammation in general [Eberhard J., 2002, Virchows Archiv, 440(6):627-634].

It has been described that in both NASH and ASH there is an alteration in the ratio keratin 18/keratin 8 [Denk H., et al., Der Pathologe, 2001, 22(6):388-398]. In addition, keratin 18 (K1CR) levels are indicators of other liver diseases such as hepatic carcinoma, chronic hepatitis, alcoholic hepatitis and cryptogenic cirrhosis [Caulin C., Journal of Cell Biology, 2000, 149(1):17-22; Toivola D. M., et al., Experimental Cell Research, 2000, 255(2):156-170; Stumptner C., et al., Hepatology, 1997, 26(4, part 2):194A; Ku Nam-On, et al., Journal of Clinical Investigation, 1997, 99(1):19-23].

Guanidinoacetate N-methyltransferase (GAMT) is a protein involved in the last step of creatinine biosynthesis. Superoxide dismutase (SODC) is a protein that destroys radicals that are toxic for cells. Albumin (ALBU) is a low molecular weight protein which is soluble in diluted saline solutions and water. It can bind water, ions (sodium, potassium or calcium), fatty acids, hormones, etc. Antioxidant protein 2 (AOP2) protects against oxidative damage. Methionine adenosyl transferase (MAT) catalyzes AdoMet formation from methionine and ATP. Long-chain acyl-CoA dehydrogenase (ACDL) is an enzyme that is involved in the mitochondrial beta-oxidation of fatty acids. Selenium binding protein (SBP) binds selenium and acetaminophen.

Prohibitin 1 (PHB1) is a protein that is associated with the inner mitochondrial membrane whose function has been related to the folding and stabilization of proteins involved in mitochondrial respiratory processes. Deficiency of PHB1 has been associated with an alteration of the mithocondrial function and to premature aging. Its relationship with liver cancer has been described [Seow T. K., et al., Electrophoresis, 2000, 21(9):1787-1813].

No relationship between the expression of the said proteins and the development of NASH has been previously established, thus, their use as molecular markers and fingerprint for NASH has turned out to be surprising.

Therefore, one aspect of this invention is a method for the collection of data that allows for the early diagnosis or confirmation of NASH, which comprises the in vitro detection and quantification of the levels of a protein selected from apolipoproten A1, mitochondrial ATPase β subunit, leukotriene $A_4$ hydrolase, keratin 18, guanidinoacetate N-methyltransferase, superoxide dismutase, albumin, antioxidant protein 2 (isoform 1), prohibitin 1, methionine adenosyl transferase, long-chain acyl-CoA dehydrogenase, selenium binding protein, antioxidant protein 2 (isoform 2) and their combinations, in a sample of liver tissue from a subject and the comparison of the obtained results with normal values, of reference, of said proteins in liver tissue obtained from healthy livers. In a particular embodiment, said protein is selected from apolipoproten A1, mitochondrial ATPase β subunit, leukotriene A4 hydrolase, keratin 18, prohibitin 1 and their combinations.

The method provided by this invention allows the easy and reliable evaluation of the potential risk of a subject to develop NASH. Said subject may be a subject who has not been previously diagnosed with NASH or a subject who has been diagnosed with NASH but wants to confirm the diagnosis. Therefore, in a particular embodiment, said method allows the evaluation of the predisposition (early diagnosis) of a subject to develop NASH, while in another particular embodiment, said method allows the confirmation (diagnosis) of the existence of NASH in a subject.

In another aspect, the invention is related to the use of a protein selected from apolipoproten A1, mitochondrial ATPase β subunit, leukotriene $A_4$ hydrolase, keratin 18, guanidinoacetate N-methyltransferase, superoxide dismutase, albumin, antioxidant protein 2 (isoform 1), prohibitin 1, methionine adenosyl transferase, long-chain acyl-CoA dehydrogenase, selenium binding protein, antioxidant protein 2 (isoform 2) and their combinations, in an in vitro method for the diagnosis of NASH, or for the evaluation of the predisposition of a subject to develop NASH.

BRIEF DESCRIPTION OF THE FIGURES

FIG. 4 is a bar chart that shows the inner mitochondrial membrane potential. Membrane functionality was studied by means of the measurement of said gradient in an enriched mitochondrial fraction from 3 month-old WT and MAT1A-/- mice livers. Value of 100% was 175,51+6,69 fluorescence units/mg protein. The average of three experiments is shown.

FIG. 5 illustrates PHB1 level regulation by AdoMet in cultured rat hepatocytes. PHB1 levels were measured in rat hepatocytes cultured for 12 or 24 hours in the presence or absence of 100 µM methionine, 4 mM AdoMet or 20 mM cycloleucine. Liver extracts (15 µg/lane) were analyzed by Western blotting using specific antibodies. To ensure equal loading, the membranes were stained with red Ponceau. A representative blot from three independent experiments is shown.

DETAILED DESCRIPTION OF THE INVENTION

In one aspect, the invention is related to an in vitro method for the diagnosis of NASH, or to evaluate the predisposition of a subject to develop NASH. A method like the one provided by this invention allows for the evaluation of the predisposition or risk of a subject to develop NASH, that is to say that permits the determination of those subjects that, within a group or population, show a higher risk of developing NASH. In an illustrative way, a subject who has not been previously diagnosed with NASH or who has no symptoms may be analyzed in order to obtain information about the possibility of that subject developing NASH in the future.

Likewise, said method might be used with diagnosis (diagnosis method) or prognostic (prognostic method) purposes. A diagnosis method refers to an assay performed on a subject who presents possible NASH symptoms. A prognostic method refers to a method that helps predict, at least at some extent, the progress of the disease. In this sense, a subject who has been previously diagnosed with NASH might be analyzed to know the progress of the disease as well as to know the possibility of a favorable response to a certain therapeutic treatment.

The term "subject" as used in the present invention includes human beings and animals, for example, mammals. In a particular embodiment, said subjects are human beings, females or males, of any age or race.

The term "non-alcoholic steatohepatitis" or "NASH" is used in the sense which is nowadays admitted by the scientific community.

In a more specific way, the invention provides a method that comprises:

a) obtaining a sample of liver tissue from a subject;

b) detecting and quantifying in said sample of liver tissue the level of a protein selected from apolipoprotein A1 (APA1), mitochondrial ATPase β subunit (ATPB), leukotriene $A_4$ hydrolase (LKHA), keratin 18 (K1CR), guanidinoacetate N-methyltransferase (GAMT), superoxide dismutase (SODC), albumin (ALBU), antioxidant protein 2 (AOP2) (isoform 1 y 2), prohibitin 1 (PHB1), methionine adenosyl transferase (MAT), long-chain acyl-CoA dehydrogenase (ACDL), selenium binding protein (SBP) and their combinations; and c) comparing the results obtained in step b) with normal values of reference for said proteins in liver tissue.

The liver tissue sample to be analyzed may be a liver tissue sample from any part of the liver of the subject whose susceptibility to develop NASH, or whose diagnosis of NASH, is intended to be known. Said liver tissue sample from said subject may be obtained by any conventional method, for example, by biopsy.

Detection and quantification in a liver tissue sample of the levels (concentration) of said proteins APA1, ATPB, LKHA, K1CR, GAMT, SODC, ALBU, AOP2 (isoform 1), AOP2 (isoform 2), PHB1, MAT, ACDL and/or SBP can be performed by the use of specific antibodies against said proteins, by ELISA or Western Blotting. Alternatively, said proteins can be detected and quantified by the use of devices of the kind of biochips or protein microarrays which include specific antibodies against proteins to be detected, for example, detection microarray systems that allow the detection and quantification of target proteins (Huang, R P. Detection of multiple proteins in an antibody-based protein microarray system. Journal of Immunological Methods 225 (2001): 1-13). The term "antibody" as used herein includes monoclonal and polyclonal antibodies, recombinant fragments of antibodies, combibodies, Fab and scFv antibody fragments as well as the ligand binding domains.

Even though, in principle, the detection and quantification of the level of just one of said proteins would be enough, in practice, it is preferable to detect and quantify the level of two or more of said proteins to obtain the fingerprint of the subject in relation to its susceptibility to develop NASH or to confirm a diagnosis of NASH.

The results obtained in step b), related to the detection and quantification of proteins APA1, ATPB, LKHA, K1CR, GAMT, SODC, ALBU, AOP2 (isoform 1), AOP2 (isoform 2), PHB1, MAT, ACDL and/or SBP in an liver tissue sample, are compared with normal values of reference for said proteins in liver tissue from healthy livers. Said reference normal values of said proteins in liver tissue may be obtained by the analysis and quantification of said proteins in liver tissue samples from healthy livers, that is to say, from livers of subjects who have not developed NASH nor any other liver disease that could originate inadequate reference values for said proteins. In general, increases or decreases in the levels of marker proteins are estimated by comparison of the results obtained from the analyses of samples from assay subjects with results obtained from control samples that are analyzed at the same time. In each assay, each subject will be compared with previously validated control samples.

When the comparison of the results obtained in step b) with reference normal values shows that:

(i) the level (concentration) of, at least, one of proteins APA1, ATPB, LKHA, K1CR, GAMT, SODC, ALBU or AOP2 (isoform 1), is higher than the highest limit of the normal values, of reference, for said proteins in liver tissue; and/or (ii) the level (concentration) of, at least, one of proteins PHB1, AOP2 (isoform 2), MAT, ACDL or SBP is lower than the lowest limit of the normal values, of reference, for said proteins in liver tissue, then, said results are indicative of the existence of NASH in the subject whose liver tissue sample has been assayed or there is a predisposition or high risk of said subject to develop NASH in the future.

A method like the one previously described allows for obtaining data for the early diagnosis of NASH or for the confirmation of NASH presence.

In a particular and preferred embodiment of the method provided by this invention, marker protein of NASH is selected from APA1, ATPB, LKHA, K1CR, PHB1 and their combinations. In this case, a level (concentration) of, at least, one of proteins APA1, ATPB, LKHA or K1CR, higher than the highest limit of the normal reference values for said proteins in liver tissue and/or a level (concentration) of PHB1 lower than the lowest limit of the normal reference values for said protein in liver tissue, is indicative of the existence of NASH in the subject whose liver tissue sample has been assayed or there is a predisposition or high risk of said subject to develop NASH in the future. Even though, in principle, the detection and quantification of the level of just one of said proteins would be enough, in practice, it is recommendable to detect and quantify the level of at least two of them, preferably three, more preferably four and even more preferably, the levels of the five mentioned proteins because that would allow for the fingerprint of the subject in relation to its predisposition to develop NASH or to confirm a diagnosis of NASH.

In another aspect, the invention is related to the use of a protein selected from APA1, ATPB, LKHA, K1CR, GAMT, SODC, ALBU, AOP2 (isoform 1), AOP2 (isoform 2), PHB1, MAT, ACDL, SBP and/or their combinations, preferably APA1, ATPB, LKHA, K1CR, PHB1, and/or their combinations, in an in vitro method to diagnose NASH, or to evaluate the predisposition of a subject to develop NASH.

The following example illustrates the invention and should not be considered in a limiting sense of the invention.

EXAMPLE 1

Proteomic Functional Analysis of Non-alcoholic Steatohepatitis (NASH)

Molecular mechanisms involved in the progression of NASH in MAT1A−/− mice livers have been studied by a high throughput proteomic approach.

1. Material and Methods 1.1. Materials

Antibodies of anti-cytochrome c oxidase subunits I and II were obtained from Molecular Probes. Anti-prohibitin 1 antibody was purchased from Calbiochem. Anti-mitochondrial ATP synthase subunit β was obtained from Molecular Probes. Electrophoresis reactants were obtained from Bio-Rad. Trypsin, from Promega; urea and collagenase from Gibco BRL; and tiourea from Merck. The other chemical reactants were purchased from Sigma.

Animals [wild type mice (WT) and knockout mutants lacking gene MAT1A (MAT1A−/−) or MATO mice (Lu S. C., et al., Proc. Natl. Acad. Sci. USA, 2001; 98:5560-5565)] came from the applicants inbred colony and were treated humanely according to the institutional guidelines of the applicants. Ob/ob mice were purchased from Jackson Laboratories (Bar Harbor, Mich.). Human samples were obtained from the Hospital Príncipe de Asturias, whose human research review committee approved this study.

1.2. Methods

High Throughput Proteomic Analysis.

Liver samples were homogenized in 20 volumes of lysis buffer which contained 7 M urea, 2 M thiourea, 4% CHAPS, 1% DTT and 0.5% Bio-Lyte 3-10 ampholytes. The homogenates were centrifuged at 100,000×g for 45 minutes at 15° C. Protein concentration was determined in the supernatants by means of the Bradford protein assay kit (Bio-Rad) using albumin diluted in lysis buffer as standard. The first separation, by isoelectrofocus, was performed in a Protean IEF cell (Bio-Rad) using 17 cm ReadyStrips IPG strips with different pH ranges. The samples (300-700 µg of protein) were loaded and an active rehydration was performed for 12 h at 50 V and 20° C. Gels were run at 60,000 Vh by using a progressively increasing protocol implemented by the manufacturer. IPG strips were equilibrated in 50 mM Tris/HCl, pH 7.5, 6 M urea, 30% glycerol, 2% SDS and 2% DTT and incubated in the same buffer containing iodoacetamide and bromophenol blue in the absence of DTT. IPG strips were directly loaded in 12.5% polyacrylamide gels (18 cm×20 cm×1 mm) and sealed with low-melting-point agarose. Gels of the second separation, by SDS-PAGE, were run for 15 h. Gels were stained with PhastGel Blue® prepared in water (65%), ethanol (25%) and acetic acid (10%). Alternatively, they were stained with silver using the Amersham silver staining kit. Images were digitized with an Image Densitometer from Bio-Rad and analyzed by using PDQuest software. Qualitative and quantitative differences were detected but they were only accepted when confirmed, at least, twice, in five independent experiments. Gel spots corresponding to differentially expressed proteins were picked up manually and processed in a Micromass MassPrep station. Gel specimens were de-stained with 50 mM ammonium bicarbonate and 50% acetonitrile (Coomassie-stained gels) or with 15 mM potassium ferricyanide and 50 mM sodium thiosulphate (Silver-stained gels). Subsequently, proteins were reduced with 10 mM DTT in 100 mM ammonium bicarbonate and were alkylated with 55 mM iodoacetamide in the same buffer. After that, a digestion of the proteins was performed in the same gel with trypsin 6 ng/µl in 50 mM ammonium bicarbonate, for 5 h at 37° C. The resulting peptides were extracted with 1% formic acid and 2% acetonitrile. Finally, 2 µl samples were mixed with 2 µl of a saturated solution of α-cyano-4-hydroxi-trans-cinnamic acid in 0.1% TFA, 50% acetonitrile and then spotted into a MALDI target plate. Fragments obtained from the digestion with trypsin were analyzed in a MALDI TOFF GL-REF mass spectrometer (Micromass). Data processing was performed with MassLynx and database searching (SWISSPROT, TREMBL, ENSEMBL) to identify the proteins of interest from their peptide fingerprint was performed with ProteinLynx Global Server (Micromass). Data analysis and clustering was performed with GARBAN (unpublished).

Isolation and Culture of Rat Hepatocytes.

Hepatocytes were isolated from male Wistar rats (200-250 g) by perfusion with collagenases, as previously described (Avila, M. A., et al., Gastroenterology, 1998, 114:364-371). Once isolated, hepatocytes were cultured according to García-Trevijano et al. (García-Trevijano, E. R., et al., Faseb J, 2000, 14:2511-2518) in the presence or absence of 4 mM AdoMet, 100 µM methionine, or 20 mM cicloleucine (CL) for the indicated periods of time. Cell viability was measured by trypan blue exclusion, and no significant differences were observed between the controls and any of the different treatments performed in this study.

Mitochondrial Isolation and Characterization.

An enriched mitochondrial fraction was obtained from 100 mg liver specimens with the Mitochondria Isolation Kit from Sigma. The electrochemical proton gradient ($\Delta\psi$) of the inner mitochondrial membrane was analyzed by measuring the uptake of the fluorescent carbocyanine dye JC-1 into the mitochondria according to the manufacturer's instructions. Fluorescence measures were performed with a Perkin Elmer LS 50 B spectrofluorimeter.

RNA Isolation and Northern Hybridization Analysis.

Total liver RNA was isolated by the guanidinium thyocianate method (García-Trevijano, E. R., et al., Faseb J, 2000, 14:2511-2518). RNA concentration was determined spectrophotometrically before use and the integrity was checked by electrophoresis with subsequent ethidium bromide staining. Electrophoresis and gel blotting were performed following a previously described protocol (Lu, S. C., et al., Proc. Natl. Acad. Sci. USA, 2001; 98:5560-5565). Prohibitin 1cDNA was cloned by reverse transcriptase-polymerase chain reaction from mouse liver. The Superscript preamplification system (Life Technologies), Taq Long plus enzyme (Stratagene) and sense 5'-atggctgccaaagtgtttgagtc-3' and antisense 5'-tcactggggaagctggagaagc-3' primers were used. Probes for ATPase β subunit and for cytochrome oxidase subunits I and II have been described (Izquierdo & Cuezva, Mol. Cell. Biob, 1997, 17:5255-5268; Otero, G., et al., Carcinogenesis, 1997, 18:1569-1575). Northern hybridization analysis were performed on total RNA by using standard procedures (Lu S. C., et al., Proc. Natl. Acad. Sci. USA, 2001; 98:5560-5565). All probes were labeled with [$^{32}$P]dCTP by using the Rediprime DNA Labeling System from Amersham. To ensure equal loading of RNA samples, membranes were also hybridized with a probe labeled with $^{32}$P rRNA 8S. Both autoradiography and densitometry were used to quantify relative RNA. Results of the Northern blot analysis were normalized to 18S rRNA.

DNA Isolation and Southern Blot Analysis.

Total DNA was extracted from the livers of 3-month-old WT and MAT1A-/- mice as previously described (34). Total cellular DNA (20 µg) was digested with EcoRI. Digested DNA was resolved in an agarose 1% gel, transferred and fixed onto nylon membranes. The membranes were incubated with a COX II probe labeled with [$^{32}$P ]dCTP. Membrane hybridization and washing conditions were described above (Otero, G., et al., Carcinogenesis, 1997, 18:1569-1575).

Western Blot Analysis.

Protein extraction and western blotting were performed as previously described (Avila, M. A., et al., Oncogene, 1995, 10:963-971; Ruiz, F., et al., Hepatology, 1998, 28:1051-1057). Briefly, equal amounts of protein (15 µg) were resolved in SDS/12.5% polyacrylamide gels. Proteins were electrophoretically transferred to nitrocellulose membranes. Membranes were probed with anti-MAT (Ruiz, F., et al., Hepatology, 1998, 28:1051-1057), anti-PHB1, anti-β ATPase and anti-COX I and II. A secondary antibody conjugated to horseradish peroxidase was used. Blots were developed by chemiluminescence (Dupont).

2. Results

Proteomic Fingerprint of NASH Pathogenesis in MAT1A-/- Mice

Molecular mechanisms involved in NASH development in MAT1A-/- mice liver have been studied by a high throughput proteomic approach. Protein expression patterns were obtained by two-dimensional analysis of 1-, 15-, 90- and 240-day-old WT and MAT1A-/- mice liver extracts. Five independent experiments were performed using liver extracts obtained from different animals. According to the PDQuest image analysis (BioRad), an average of 1,500 to 2,000 spots were visualized depending on the gel staining procedure. Gel images obtained from WT and MAT1A-/- mice were compared to determine differences in protein expression. Only those changes in which a two-fold increase or a decrease by half was confirmed in the five experiments were accepted.

Analysis revealed that just 1 day after birth, 140 differences were already induced in the liver of MAT1A−/− mice and that changes accumulated with age (242, 259 and 297 changes 15, 90 and 240 days after, respectively). The distribution between up-regulated and down-regulated proteins is maintained up to three months. 53%-70% were up-regulated and 30%-47% were down-regulated proteins. In contrast, this pattern switches in 8-month-old MAT1A−/− mutant mice livers, when NASH is already developed, where 27% were up-regulated and 73% were down-regulated proteins. From all the initial changes, only the most abundant proteins represented in the databases were identified by peptide mass fingerprinting, with a result of 117 proteins successfully identified.

A linear correlation between $M_r$ and pI, calculated from the sequence of the identified proteins, and the experimental Rf of the corresponding spot, calculated from the two-dimensional gels (not shown), has been found. This finding further validates the identity of the analyzed spots. Some pI deviations from linearity were observed. This is probably a consequence of post-translational modifications.

Figure 1:
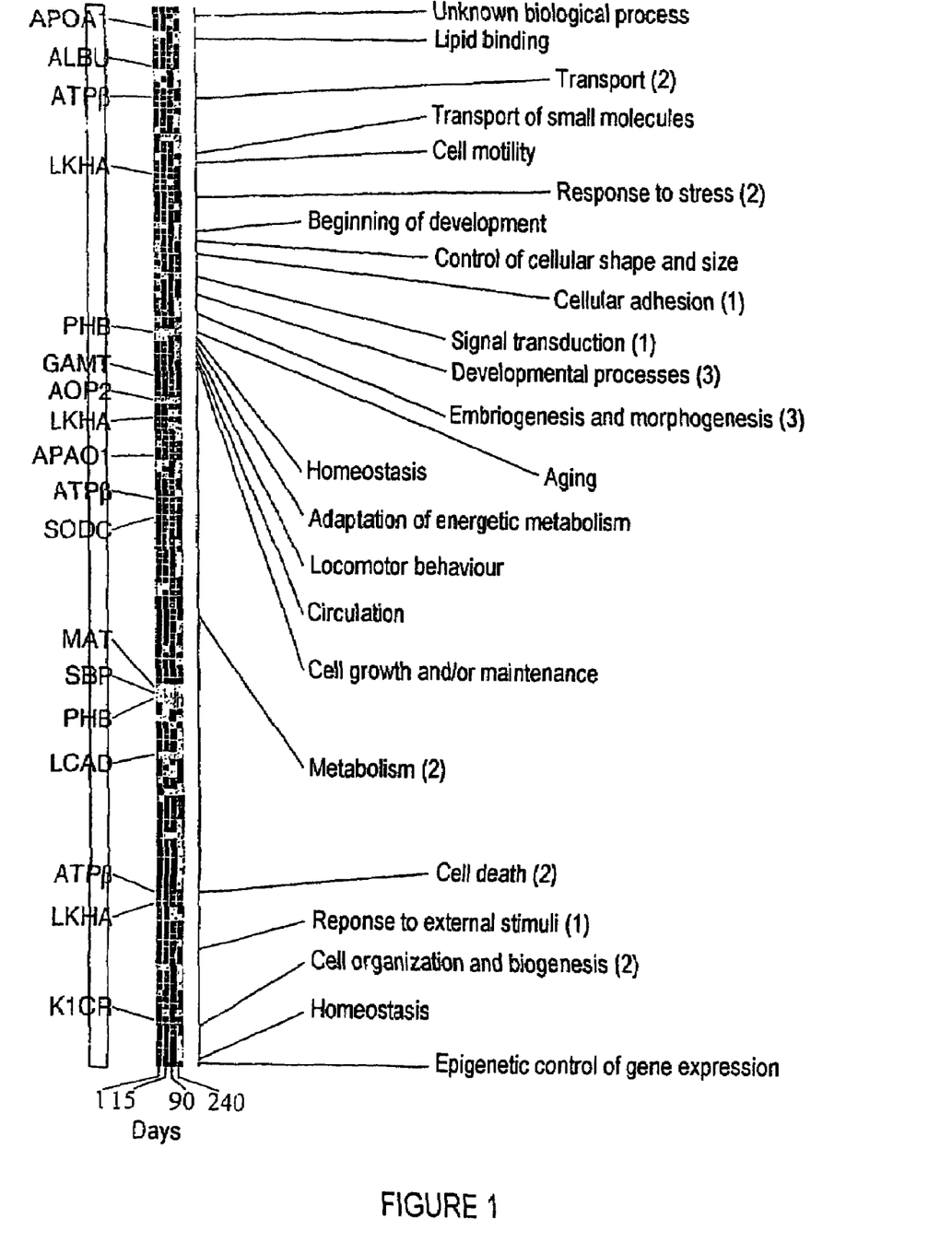
FIG. 1 shows the list of the proteins differentially expressed in MAT1A-/- mutant mice during the development of NASH. Liver extracts from 1-, 15-, 90- and 240-day-old WT and MAT1A-/- mice were analyzed by two-dimensional electrophoresis. Proteins differentially expressed were identified by MALDI TOFF mass spectrometry and clustered by the biological processes in which they are involved according to gene ontology criteria: (1) Cell communication; (2) Cell growth and/or maintenance; (3) Developmental processes.
Figure 2:
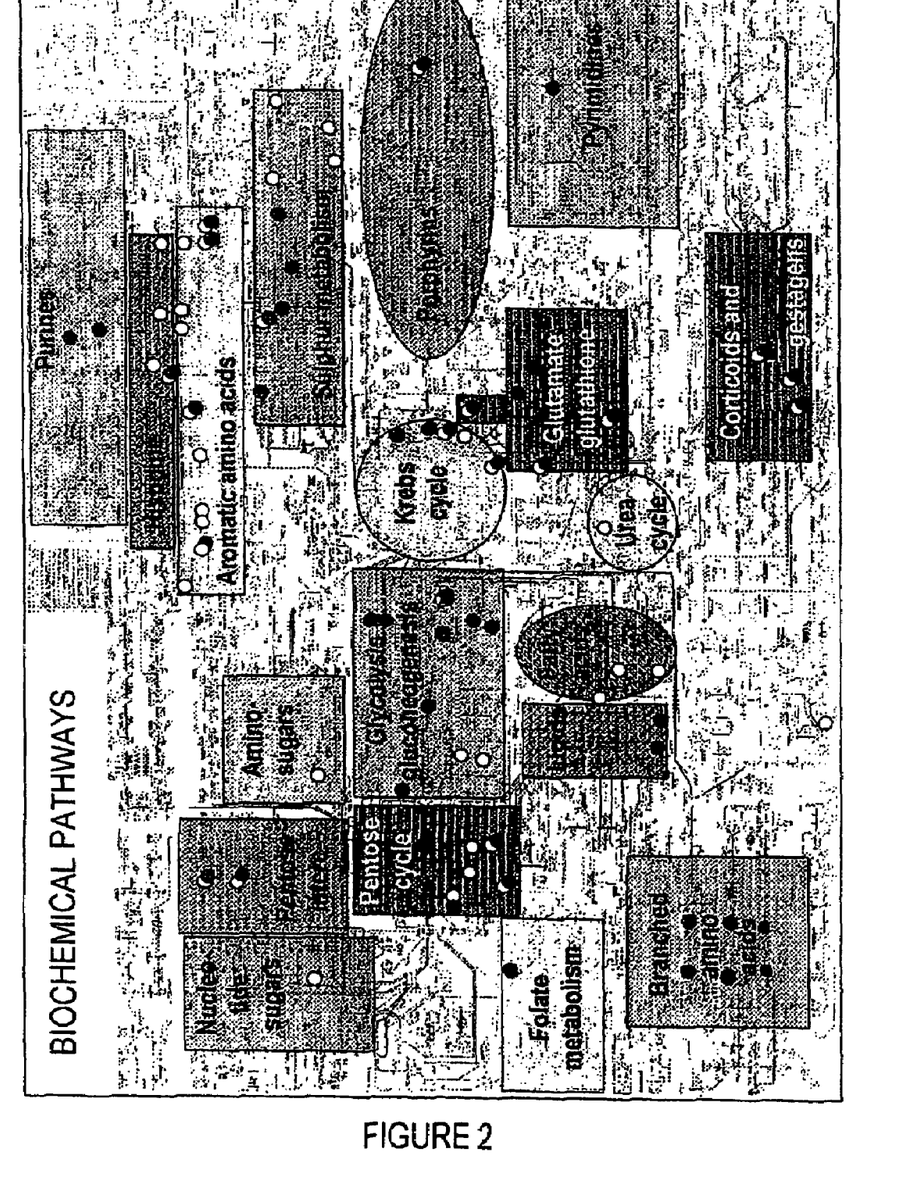
FIG. 2 is a chart that illustrates the metabolic alterations of MAT1A-/- mutant mice livers during the progression of NASH. Metabolic enzymes which were up- or down-regulated in the liver of 1-, 15-, 90- and 240 day-old MAT1A-/- mutant mice were mapped in the wall chart "Biochemical Pathways" of Boehringer Mannheim (http://www.expasy.org) using the program GARBAN developed in the University of Navarra.

The specific protein expression profile of MAT1A−/− mice livers provides a proteomic fingerprint of NASH. Up- and down-regulated proteins were classified by the biological processes in which they are involved according to the gene ontology criteria, and were represented as shown in FIG. 1. Most proteins differentially expressed in MAT1A−/− mutant mice livers were clustered in three biological processes: cell communication (group 1), cell growth and/or maintenance (group 2) and developmental processes (group 3) (FIG. 1). Some of the proteins identified in these clusters are involved in embryogenesis, morphogenesis and aging processes, such as tubulin α-6 chain, tubulin α-5 chain, actin and prohibitin 1 (PHB1), that controls DNA synthesis and regulates cell proliferation. Likewise, proteins involved in stress responses, such as leukotriene $A_4$ hydrolase (LKHA), are up-regulated. Changes in the expression pattern of proteins involved in oxidative stress were also identified, for example, glutathione peroxidase, antioxidant protein 1 and 2 (AOP2) or superoxide dismutase Cu++/Zn++ (SODC). Finally, according to the broad metabolic activity of the liver, 80% of the proteins whose expression changes in MAT1A−/− mutant mice corresponds to metabolic proteins. Most of the alterations affect carbohydrate and amino acid metabolism. For example, fructose 1,6-bisphosphatase (up-regulated) and glycerol 3 phosphate dehydrogenase (down-regulated) are key enzymes in gluconeogenesis and glycolysis respectively. Specific long-chain acyl-CoA dehydrogenase (ACDL) and delta 3,5 delta 2,4 dienoyl CoA isomerase (both down-regulated) are involved in fatty acid beta-oxidation. Apolipoprotein A1 (APA1) (up-regulated) and farnesyl pyrophosphate synthetase (down-regulated) take part in the transport and biosynthesis of cholesterol respectively; and malate dehydrogenase and isocitrate dehydrogenase (both down-regulated) catalyze two steps of the citrate cycle. In addition, major differences affecting branched, aromatic and sulfur amino acid metabolism were identified (FIG. 2).

A group of 12 proteins changed their expression pattern 1 day after birth and this alteration was maintained all along the progression of NASH in MAT1A−/− mice livers (FIG. 1). These proteins, which might be considered as early markers of NASH, were identified as APA1, LKHA, selenium binding protein (SBP), AOP2, MAT, keratin type 1 cytoskeletal 18 (K1CR), guanidinoacetate metiltransferase (GAMT), PHB1, SODC, albumin, ACDL and mitochondrial ATPase β subunit (ATPB). Most of these proteins are metabolic enzymes or take part in the antioxidant response of MAT1A−/− mutant mice hepatocytes. Interestingly, PHB1 and ATPB are mitochondrial proteins, so changes on their expression might compromise mitochondrial function.

AdoMet Regulates a Network of Mitochondrial Proteins and Mitochondrial Function.

Figure 3:
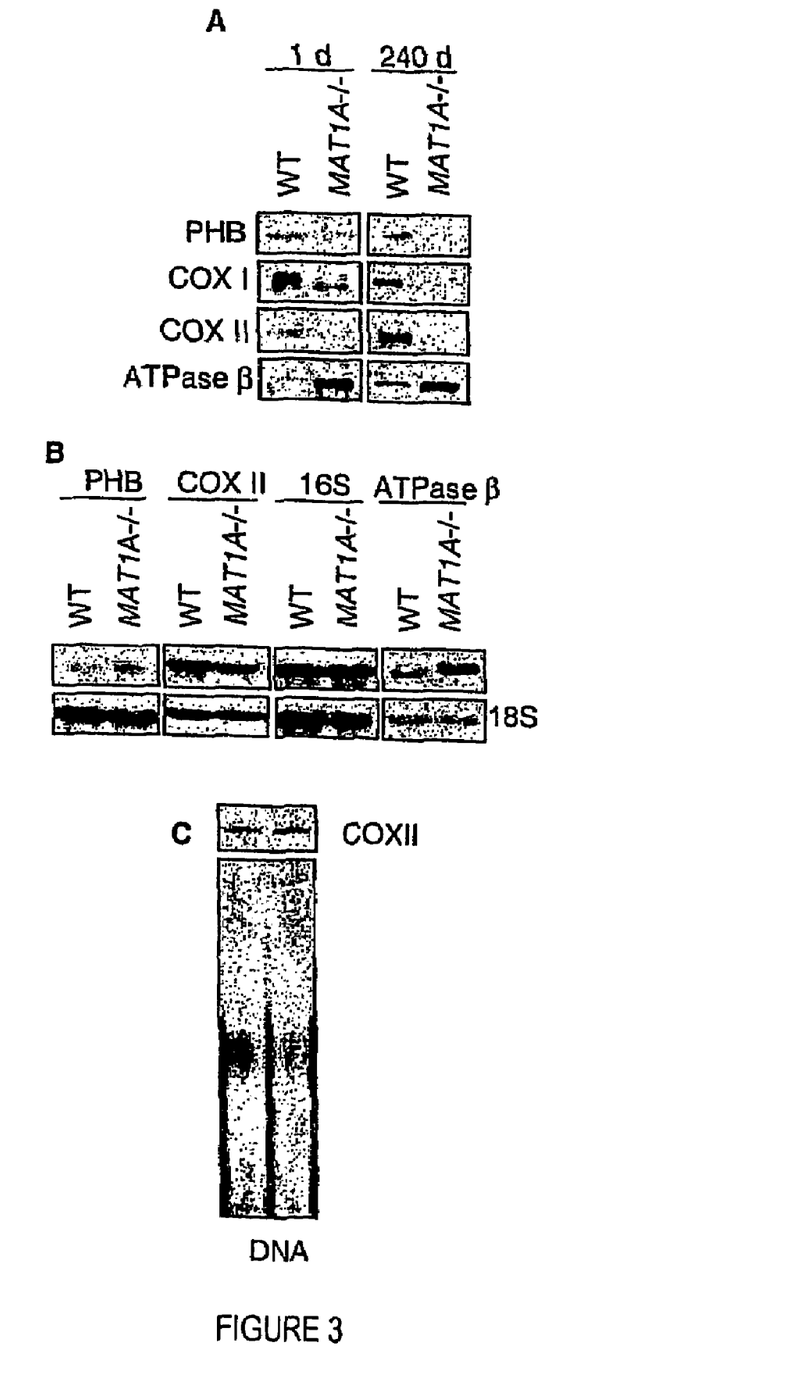
FIG. 3A shows the results of a Western blot analysis, more specifically, it shows hepatic levels of PHB1, COX I, COX II, ATPB, in a steady state, in WT y MAT1A-/- mice livers. 1 to 240 day-old mice liver extracts (15 µg/lane) were analyzed by Western blotting. To ensure equal loading, membranes were stained with Poinceau Red.
FIG. 3B shows the results of a Northern blot analysis, more specifically of the expression of PHB1, COX II, ATPB, and rRNA 16S in WT and MAT1A-/- mice livers. Samples of liver RNA (30 µg/lane) from 90 day-old mice were analyzed by a Northern blot hybridization analysis using specific probes. Membranes were hybridized with a probe for rRNA 18S to ensure equal loading.
FIG. 3C shows the results of a Southern analysis, more specifically of mitochondrial DNA in MAT1A-/- mice in relation to WT mice. Total DNA was isolated from 3 month-old mice, cleft with EcoRI and used in a Southern analysis with a specific probe for COX II. Equal loading of DNA samples in each of the lanes was ensured by ethidium bromide staining of the gel. Representative blots from three independent experiments are shown.

Alteration of the mitochondrial function may be a key factor in the progression of NASH in MAT1A−/− mice. Up-regulation of ATPB (450%) and down-regulation of PHB1 (53%) were confirmed by Western blot analysis with specific antibodies (FIG. 3A). Likewise, the steady state levels of cytochrome c oxidase subunits I and II (COX) were also diminished in MAT1A−/− mutant mice livers (55% and 53% respectively). These alterations were not observed in other tissues (not shown). The expression of genes which encode for these proteins was also studied by Northern blot analysis. The mRNA level of ATPB is increased two-fold in MAT1A−/− mice livers (FIG. 3B). On the contrary, mRNA levels of PHB1 and COX II, as well as of rRNA 16S, were similar to those found in WT mice (FIG. 3B). These observations indicate that the down-regulation in PHB1 and COX by AdoMet involves post-translational mechanisms. Whereas PHB1 is the product of a nuclear gene, COX subunits are encoded by mitochondrial genes. Additionally, no changes were observed in mitochondrial DNA content in MAT1A−/− mice livers (FIG. 3C). Changes in the expression pattern of PHB1, COX and ATPB proteins suggest a deficiency in mitochondrial respiratory processes.

Figure 4:
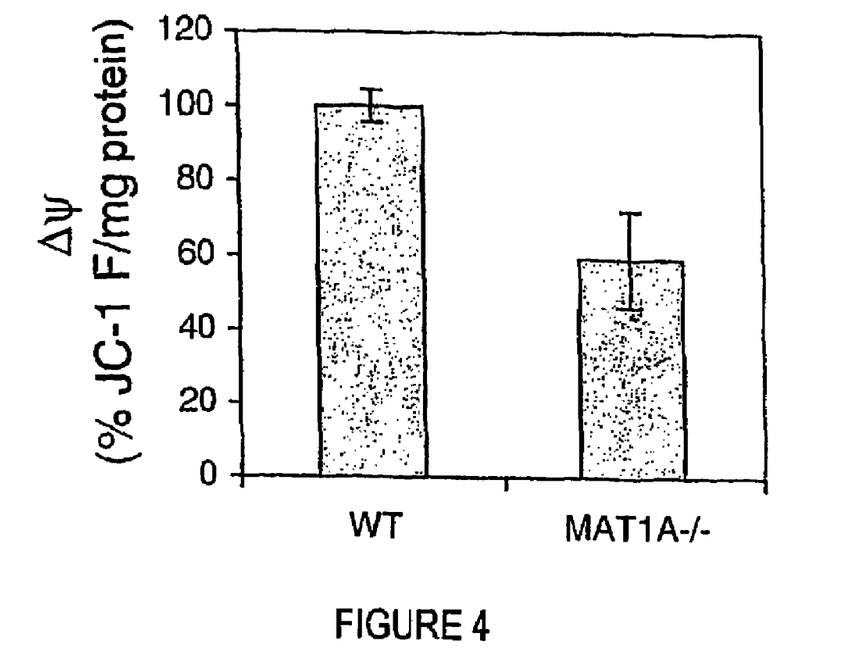

The inner mitochondrial membrane potential was measured in an enriched mitochondrial fraction purified from WT and MAT1A−/− mice liver extracts. A 40% reduction was assessed on the electrochemical proton gradient in MAT1A−/− mutant mice liver extracts (FIG. 4), indicating a deficiency of the inner mitochondrial membrane integrity.

Regulation of PHB1 by AdoMet

Figure 5:
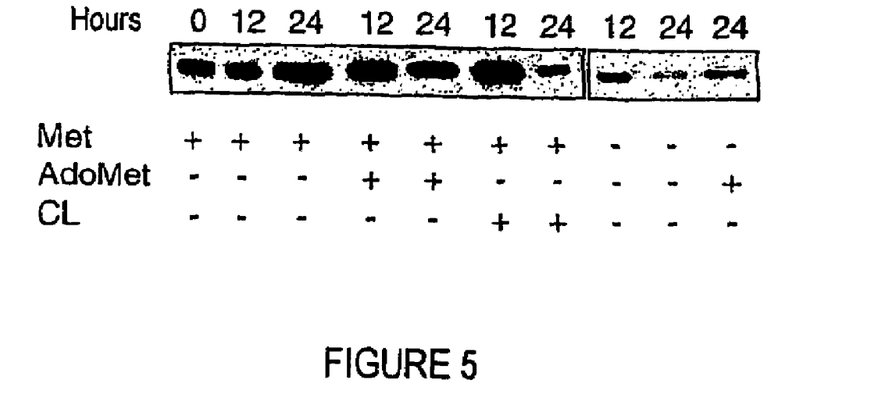

The possibility of the regulation of PHB levels in cultured hepatocytes of rat by AdoMet was studied. In the presence of methionine or AdoMet in the culture media, no effect was detected on PHB1 levels after 24 h incubation under standard conditions (FIG. 5). However, impairment of AdoMet synthesis by restriction of methionine or addition of CL to the culture medium (a well known inhibitor of MAT activity) was observed, resulting in the down-regulation of PHB1 (53% and 55% respectively) (FIG. 5). Restoration of hepatocyte intracellular pool of AdoMet by exogenous addition of this compound after 12 hours culture in the absence of methionine, prevented the decrease of PHB1.

Figure 6:
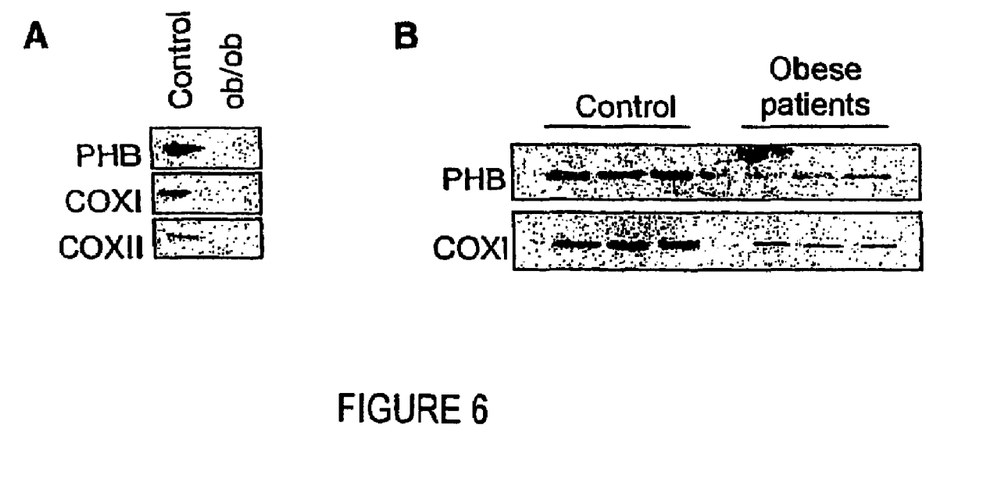
FIG. 6A shows hepatic steady-state levels of PHB1, COX I and COX II in WT and ob/ob mice livers. A representative blot from three independent experiments is shown.
FIG. 6B shows hepatic steady-state levels of PHB1 and COX I in control and obese patient livers. Liver extracts (15 µg/lane) were analyzed by Western blotting using specific antibodies. To ensure equal loading, the membranes were stained with red Ponceau.

AdoMet Deficiency and Mitochondrial Alterations in Ob/Ob Mice and Obese Patients In order to evaluate whether the alterations observed in MAT1A−/− mice provide new mechanisms of NASH induction, the steady state levels of PHB1 and COX were studied in ob/ob mice liver samples and in obese patients, two conditions which favor the development of NASH. Western blot analyses revealed that PHB1 and COX I, II are down-regulated in ob/ob mice livers (76% and 81% and 70% respectively). Down-regulation of PHB1 (53%) and COX I (82%) was also confirmed in obese patient livers although COX II levels were similar to those found in control livers (FIG. 6). As in MAT1A-/- mice, mRNA levels of PHB and COX I and II in ob/ob mice and obese patients are correlated with the levels found in non-control animals (not shown).

3. Discussion

AdoMet has been generally considered as an intermediary central metabolite involved in the synthesis of homocysteine and polyamines as well as the main cellular methyl group donor. However, recent findings evidence that, in addition to this central metabolic function, AdoMet is a cellular control switch that regulates essential hepatocyte functions such as proliferation, differentiation and death (Mato, J. M. et al., Faseb J, 2002, 16:15-26). In order to better understand the mechanisms by which these non-traditional AdoMet functions take place, NASH pathogenesis was studied in mutant MAT1A-/- mice deficient in hepatic AdoMet synthesis by using a high throughput proteomic approach.

The analysis of the different protein expression patterns in MAT1A-/- and WT mice indicates that a chronic deficiency in the synthesis of AdoMet has a pleiotropic effect in the liver altering essential hepatic functions. 117 proteins which are differentially expressed in MAT1A-/- mice livers during NASH progression have been identified. The global analysis of the observed differences shows up-regulation of the expression of antioxidant proteins (SODC, catalase, glutathione peroxidase) in MAT1A-/- mice livers that might reflect an adaptation mechanism to dissipate oxidative stress generated by oxidant genes. Major metabolic alterations were also found in the expression of proteins in mutant MAT1A-/- mice livers. Lipid, carbohydrate and amino acid metabolism is impaired in MAT1A-/- mice from their birth, although the differences accumulate during NASH progression. These up- and down-regulated proteins provide an specific proteomic pattern. This pattern might explain some of the metabolic alterations reminiscent of those found in obesity and other conditions associated to NASH, which lead to the development of cirrhosis and HCC (Ried, A. E., Gastroenterology, 2001, 121:710-723; Angulo, P., N. Engl. J. Med., 2002, 346:1221-1231; Clark, J. M., et al., Gastroenterolgy, 2002, 122:1649-1657).

The analysis of the 117 proteins differentially expressed in MAT1A-/- mice livers revealed that most of the changes observed 1 day after birth are not maintained during NASH progression. These time-dependent differences may reflect the adaptation of the hepatocyte to perform its normal biological function under a chronic AdoMet deficiency, leading to an accumulation of alterations that condition the development of the disease. However, 12 proteins change their expression pattern after birth when MAT1A-/- is switched on in WT mice, and this alteration is maintained to the onset of histological lesions. Among these early changes are the up-regulation of SODC and AOP2, which was deduced from two-dimensional gels according to previous evidences (Rabilloud, T., et al., J. Biol. Chem., 2002, 277: 19396-19401), as well as the down-regulation of ACDL and up-regulation of APA1 may be mentioned. These alterations agree with the implication of the oxidative stress and abnormal lipid metabolism in the pathogenesis of fatty liver disease. Interestingly, 4 proteins involved in mitochondrial function were also identified: ATPB, COX I, COX II and PHB1. Up-regulation of ATPB has been implicated in mitochondrial maturation and in cell neoplasic transformation, which is consistent with the proliferative and dedifferentiated state of MAT1A-/- hepatocytes. Down-regulation of COX indicates a deficient transference of electrons to oxygen, the last step in the mitochondrial electron transference chain and due to this, provides a molecular explanation for the oxidative stress found in MAT1A-/- livers. The fall in PHB1 steady state levels might explain down-regulation of COX. PHB1 is the product of a nuclear gene which is associated to the inner mitochondrial membrane. PHB1 has been recently proposed to be a chaperone-type protein which takes part in the correct folding and assembly of some components of the mitochondrial respiratory chain. According to this hypothesis, a deficiency in PHB1 may impair the native and functional organization of respiratory proteins which are later degraded by mitochondrial proteases, compromising mitochondrial functionality. This is the reason why a decrease in PHB1 might induce a reduction of COX with the concomitant loss of mitochondrial function in MAT1A-/- hepatocytes.

Correlation between a deficiency in AdoMet synthesis and the down-regulation of PHB1 found in MAT1A-/- mice was confirmed by the in vitro experiments on isolated rat hepatocytes. The reduction in the synthesis of AdoMet by using a culture medium without methionine or with CL, an inhibitor of MAT activity, results in the down-regulation of PHB1. The replenishment of the AdoMet content in hepatocytes prevented the fall of PHB1.

PHB1 steady state levels also decreased in ob/ob mice livers and in obese patients, who are prone to develop NASH. NASH is a chronic disorder with an increasing prevalence in the population, thus becoming one of the priorities of clinic hepatology. Even though NASH pathogenesis is poorly known, the present evidence supports the existence of mitochondrial alterations which are correlated with oxidative stress as one of the most important factors. Down-regulation of PHB1 and COX induced by a chronic deficiency of AdoMet, may provide a new molecular mechanism involved in NASH pathogenesis. The results obtained for MAT1A-/- mice, indicate that PHB1 and COX levels fell long before the manifestation of any histological symptom of the disease and, therefore, may be useful in the early diagnosis and treatment of NASH.

In summary, the obtained results provide a new mechanism by which a deficiency in AdoMet adversely affects mitochondrial function and generates an oxidative stress in the liver. The fall of PHB1 levels under a chronic lack of AdoMet which leads to mitochondrial failure and to abnormal metabolism of lipids, carbohydrates and amino acids might partially explain the pathogenesis of NASH.

What is claimed is:

1. An in vitro method for assessment of a liver tissue sample from a subject, to determine presence of NASH in said subject, said method comprising:
    a) detecting and quantifying in said liver tissue sample the level of each of the following proteins: apolipoprotein A1 (APA1), mitochondrial ATPase 13 subunit (ATPB), leukotriene A4 hydrolase (LKHA), keratin 18 (K1CR), guanidinoacetate N-methyltransferase (GAMT), superoxide dismutase (SODC), albumin (ALBU), antioxidant protein 2 (AOP2) (isoforms 1 and 2), prohibitin 1 (PHB1), methionine adenosyl transferase (MAT), long-chain acyl-CoA dehydrogenase (ACDL), selenium binding protein (SBP);
    b) comparing the results obtained in step a) with normal reference values for said proteins in liver tissue; and
    c) based on said comprising, determining the presence of NASH in said subject.

2. A method according to claim 1, further comprising the step of obtaining the liver tissue sample from said subject.

3. A method according to claim 1, in which said subject is a human being.

4. A method according to claim 1, in which the detection and quantification of said proteins comprising APA1, ATPB, LKHA, K1CR, GAMT, SODC, ALBU, AOP2 (isoform 1), AOP2 (isoform 2), PHB1, MAT, ACDL and SBP is performed by means of the use of specific antibodies against said proteins.

5. A method according to claim 4, in which said antibodies comprise antibodies selected from the group consisting of monoclonal antibodies, polyclonal antibodies, recombinant fragments of antibodies, combibodies and fragments of Fab or scFv of specific antibodies against said proteins.

6. A method according to claim 1, in which the detection and quantification of said proteins comprising APA1, ATPB, LKHA, K1CR, GAMT, SODC, ALBU, AOP2 (isoform 1), AOP2 (isoform 2), PHB1, MAT, ACDL and SBP is performed by ELISA or Western blotting techniques, or by the use of devices comprising biochips or protein microarrays that include specific antibodies against the proteins to be detected.

7. A method according to claim 1, in which when the comparison of the results obtained in step a) with normal values, of reference, indicates that:
(i) the concentration of the proteins APA1, ATPB, LKHA, K1CR, GAMT, SODC, ALBU or AOP2 (isoform 1), is higher than the normal reference values for said proteins in liver tissue; and/or
(ii) the concentration of the proteins PHB1, AOP2 (isoform 2), MAT, ACDL or SBP is lower than the lowest limit of the normal values of reference for said proteins in liver tissue,
then, said results are indicative of the existence of NASH in the subject whose liver tissue sample has been assayed.

8. A method of assessing a subject to identify the presence of NASH in said subject, said method comprising: detecting and quantifying levels of each of a combination of proteins in liver tissue of said subject, said combination including the following proteins: apolipoprotein A1 (APA1), mitochondrial ATPase 13 subunit (ATPB), leukotriene A4 hydrolase (LKHA), keratin 18 (K1CR), guanidinoacetate N-methyltransferase (GAMT), superoxide dismutase (SODC), antioxidant protein 2 (AOP2) (isoforms 1 and 2), prohibitin 1 (PHB1), methionine adenosyl transferase (MAT), long-chain acyl-CoA dehydrogenase (ACDL), and selenium binding protein (SBP);
comparing levels of each of said combination of proteins to reference values that permit existence of NASH in said subject to be assessed;
and identifying from said comparing, the presence of NASH in said subject.

* * * * *

UNITED STATES PATENT AND TRADEMARK OFFICE
CERTIFICATE OF CORRECTION

| | | |
|---|---|---|
| PATENT NO. | : 7,314,720 B2 | Page 1 of 1 |
| APPLICATION NO. | : 10/540212 | |
| DATED | : January 1, 2008 | |
| INVENTOR(S) | : José Maria Mato De La Paz et al. | |

It is certified that error appears in the above-identified patent and that said Letters Patent is hereby corrected as shown below:

Column 9, line 13: "PhastGel Blue®" should be -- PhastGel Blue R --.

Column 14, line 52 (claim 1), "ATPase 13" should be -- ATPase β --.

Column 16, line 13 (claim 8), "ATPase 13" should be -- ATPase β --.

Signed and Sealed this

Sixth Day of May, 2008

JON W. DUDAS
*Director of the United States Patent and Trademark Office*